(12) United States Patent
Fukuzumi

(10) Patent No.: US 6,181,808 B1
(45) Date of Patent: Jan. 30, 2001

(54) LIVING BODY DISCRIMINATING APPARATUS

(75) Inventor: Shinichi Fukuzumi, Tokyo (JP)

(73) Assignee: NEC Corporation, Tokyo (JP)

( * ) Notice: Under 35 U.S.C. 154(b), the term of this patent shall be extended for 0 days.

(21) Appl. No.: 09/124,003

(22) Filed: Jul. 29, 1998

(30) Foreign Application Priority Data

Jul. 29, 1997 (JP) .................................................. 9-203404

(51) Int. Cl.[7] .................................................... G06K 9/00
(52) U.S. Cl. ............................................................ 382/126
(58) Field of Search ............................ 38/116, 119–127; 702/19, 64, 75–78; 356/71; 340/825.34; 324/71.1, 76.19, 76.21

(56) References Cited

U.S. PATENT DOCUMENTS

| | | | |
|---|---|---|---|
| 4,290,052 | * 9/1981 | Eichelberger et al. | 340/365 C |
| 4,394,773 | * 7/1983 | Ruell | 382/4 |
| 4,695,827 | * 9/1987 | Beining et al. | 340/365 P |
| 5,635,723 | * 6/1997 | Fujieda et al. | 250/556 |
| 5,953,441 | * 9/1999 | Setlak | 382/124 |
| 5,990,804 | * 11/1999 | Koyama | 340/825.34 |
| 6,002,786 | * 12/1999 | Hallibert et al. | 382/124 |

FOREIGN PATENT DOCUMENTS

| | | | |
|---|---|---|---|
| 61-182174 | 8/1986 | (JP) | G06K/9/00 |
| 62-74173 | 4/1987 | (JP) | G06K/9/20 |
| 1-233556 | 9/1989 | (JP) | G06F/15/30 |
| 2-1243 | 1/1990 | (JP) | A61B/5/117 |
| 2-133892 | 5/1990 | (JP) | G06K/9/00 |
| 3-266186 | 1/1991 | (JP) | G06F/15/62 |
| 3-53385 | 3/1991 | (JP) | G06F/15/62 |
| 3-87980 | 4/1991 | (JP) | G06F/15/62 |
| 3-87981 | 4/1991 | (JP) | G06F/15/62 |
| 3-46874 | 7/1991 | (JP) | G06K/9/00 |
| 3-46875 | 7/1991 | (JP) | G06K/9/36 |
| 4-241680 | 8/1992 | (JP) | G06F/15/64 |
| 6-187430 | 7/1994 | (JP) | G06F/15/62 |

* cited by examiner

*Primary Examiner*—Leo H. Boudreau
*Assistant Examiner*—Brian P. Werner
(74) *Attorney, Agent, or Firm*—Foley & Lardner

(57) ABSTRACT

When a finger 8 is put on a fingerprint input sensor 1, it is held in contact with living body potential deriving electrodes $2_1$ and $2_2$. In addition, a finger portion near the first joint is held in contact with a living body grounding electrode 3 to ground the living body. With the finger 8 pushed against the fingerprint input sensor 1 for inputting the fingerprint, finger muscle potentials signals 101 to 103 are obtained from these electrodes. A living body data measuring unit 4 takes differences of these finger muscle potentials for one another, and outputs the result as living body data potential data 104. A living body data analyzing unit 5 analyzes the potential data and frequency data of the living body potential difference data 104, and outputs analysis data 105. A living body discriminating unit 6 makes a determination, from the analysis data 105, as to whether the finger 8 is a finger of living body or a replica finger.

8 Claims, 8 Drawing Sheets

LIVING BODY DISCRIMINATING APPARATUS

BACKGROUND OF THE INVENTION

The present invention relates to a living body discriminating apparatus.

A person check is performed by extracting a person's feature quantities by using fingerprint, voiceprint, face image, etc. These data are peculiar to every person, and the recognition rate is extremely increased by dealing with increased resolution digital data. However, there is a possibility that data which is not obtained from a person, i.e., forged data, may be erroneously recognized in case of checking artificial digital data. To solve this problem, such means as one in which a check as to whether the checked data of living body is performed by also taking daily life data, or one in which oral questions concerning the pertinent person are made when inputting data. A method as the former means is disclosed in, for instance, Japanese Patent Laid-Open Publication No. 4-241680. In this method, when inputting fingerprint, various excitements are given to the finger. If the finger is of a living body, it responds to the excitements sensed by it. Other methods as the former means are disclosed in Japanese Patent Laid-Open Patent Application No. 6-187430. These methods are to check the pulsation, blood pressure, etc. by using pressure sensor and to detect infrared rays emitted from the finger by using an infrared sensor. A method as the latter means is disclosed in Japanese Patent Laid-Open Publication No. 1-233556. In this method, it is verified that the subject person is living, i.e., exists, by giving him or her instructions.

However, in the method disclosed in Japanese Patent Laid-Open Publication No. 4-241680, in which when inputting the fingerprint various excitements are given to the finger and, if the finger is of a living body, it responds to the excitements sensed by it, the responding means is left to the will of the subject person. Therefore, the subject of the fingerprint check need not be the pertinent person, and this means that forging is possible. In the methods disclosed in Japanese Patent Laid-Open Application No. 6-187430, i.e., one in which the pulsation, blood pressure, etc. are checked by using a pressure sensor, and one in which infrared rays emitted from finger are detected by using an infrared sensor, also have problems. In the case of using the pressure sensor, signals involved are simple. Therefore, even in case of any thing other than living body it is possible to provide pulsation data or blood pressure data to the pressure sensor by applying pressure thereto. In the case of the infrared ray detection method, forging is also possible by mounting, for instance, an infrared radiator on the replica finger. In the method of verifying the subject person by giving him or her instructions, the living body is known as such in the stage of the oral questions. The method, therefore, is an auxiliary means for checking the pertinent person.

SUMMARY OF THE INVENTION

An object of the present invention is therefore to provide a living body discriminating apparatus, which can verify that input data is not artifically reproduced data but data directly obtained from a living body.

According to the present invention, there is provided a living body discriminating apparatus comprising: fingerprint input sensor means on which a finger is placed when inputting fingerprint; a plurality of living body potential deriving means disposed as transparent sensors on the surface of the fingerprint input sensor means for measuring the potential difference between two muscle points of the finger; living body grounding electrode means provided on the fingerprint input sensor means for grounding the living body; living body data measuring means for amplifying signals obtained from the living body potential deriving means and the living body grounding electrode means; living body data analyzing means for performing potential measurement and frequency analysis of living body data obtained in the living body data measuring means by digitizing the data; and living body discriminating means for discriminating whether the data obtained by processing in the living body data analyzing means is of the living body.

Three elements are provided as the living body potential deriving means, two of the three elements being used to measure the potential difference between two muscle points of the finger, the remaining one of the elements being used as a living body grounding electrode. The fingerprint input sensor means has a finger guide for holding the finger at a constant position.

According to another aspect of the present invention, there is provided a living body discriminating apparatus comprising: a fingerprint sensor on which a finger is placed for inputting a fingerprint of the finger; at least two living body potential deriving electrodes provided on a surface of the fingerprint input sensor, for measuring the potential difference between two points of the muscle of the finger; a living body grounding electrode disposed on the fingerprint input sensor, for grounding the living body; a living body data measuring unit for amplifying signals obtained from the living body potential deriving units and the living body grounding electrode; a living body data analyzing unit for digitizing and frequency analyzing living body data measured in the living body data measuring unit; and a living body discriminating unit for discriminating whether obtained data is of a living body based on the analyzed result of the living body data analyzing unit.

The living body potential deriving electrodes and the living body grounding electrode are formed from a conductive oxide compound. The living body data measuring unit measures differences of the signals from the two living body potential deriving electrodes and the living body grounding electrode, and a difference between the two differences. The discrimination of the living body discriminating unit is performed based on the voltage amplitude and frequency range of the analyzed result of the living body data analyzing unit. The voltage range is 10 $\mu$V to 10 mV and the frequency is 2 Hz to 2 kHz. The discrimination is performed when the potential data exceeds the level for the trigger and does not exceed the threshold level within a predetermined time period. The frequency data is obtained by removing a power spectrum in a particular frequency band from the overall power spectrograph. At least three living body potential deriving electrodes are mounted on fingerprint input sensor. At least three living body potential deriving electrodes are mounted on fingerprint input sensor. The fingerprint input sensor unit has a finger guide for holding the finger at a constant position. The living body potential deriving electrodes is transparent.

By using a plurality of living body potential deriving electrodes and a living body grounding electrode, it is possible to obtain a finger muscle potential chart. The finger muscle potential chart shows potential vibrations and base line level variations according to the finger movement, as is made obvious in, for instance, "Muscle Motion Control", Shokodo Co., Ltd., pp. 18–22.

With the present apparatus, discrimination as to whether a finger for inputting fingerprint is of living body may be performed by using a muscle potential chart, which is obtained from the sole operation when inputting the fingerprint. The direction of waveform variation in the chart is positive or negative depending on the polarities of the living body potential deriving electrodes. However, this data cannot be known by the person who inputs the fingerprint. This means that it is impossible to input forged signal from the outside. In addition, with transparent glass electrodes provided on the fingerprint input sensor, it is possible to hold the finger in contact with the electrodes without interrupting the fingerprint input. The discrimination as to whether the finger is of living body, can be obtained by measuring and analyzing living body data obtained by using the electrodes. This means which uses a muscle potential chart, permits prevention of inputting forged fingerprint more reliably compared to the case of utilizing other living body data.

Specifically, two spaced-apart transparent glass electrodes are provided on the fingerprint input sensor, and also a glass or metal grounding electrode is provided thereon at a position to be touched by the first joint of the finger. When inputting a fingerprint, the glass electrodes and grounding electrode are touched by the finger, and it is thus possible to measure muscle potential when the finger is pushed against the sensor. With finger of living body, the muscle potential is about 100 $\mu$V to 2 mV. With a replica finger, on the other hand, noise signal of about 10 mV to 100 mV is detected. In addition, when a high electric conductivity material such as a metal is used, the potential is extremely reduced according to its resistance. Furthermore, the living body finger has a broad frequency band of about 2 Hz to 2 kHz, but the replica finger has only a frequency band corresponding to vibrations of a man holding the replica, i.e., up to about several 10 Hz.

By utilizing the potential and frequency data obtained form the electrodes in the above way, it is possible to make discrimination as to whether the finger put on the fingerprint input sensor is of living body.

Other objects and features will be clarified from the following description with reference to attached drawings.

PREFERRED EMBODIMENTS OF THE INVENTION

Preferred embodiments of the present invention will now be described will now be described with reference to the drawings.

Figure 1:
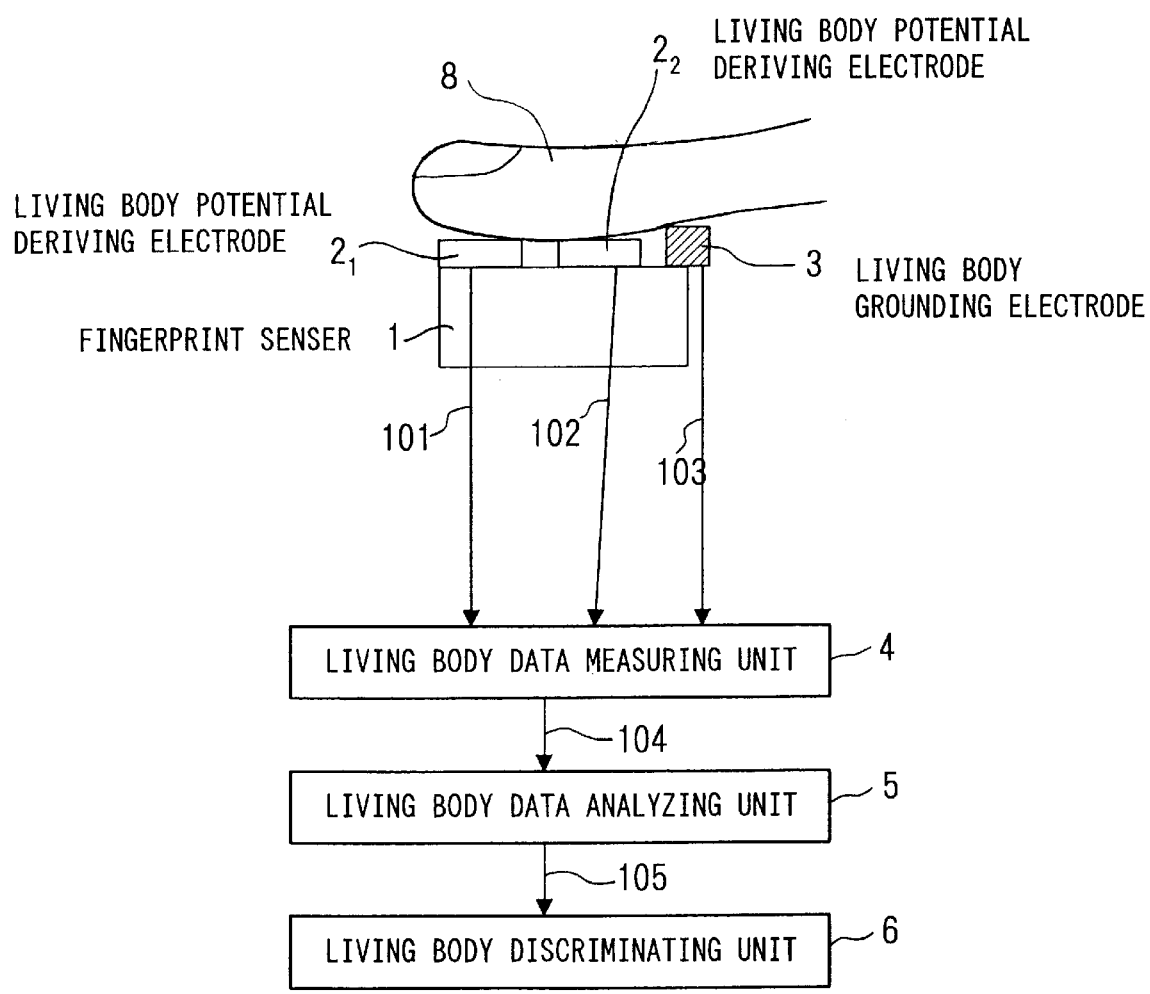
FIG. 1 is a schematic representation of a first embodiment of the living body discriminating apparatus according to the present invention.

FIG. 1 shows an embodiment of the living body discriminating apparatus according to the present invention. As shown, the apparatus comprises a fingerprint sensor 1 on which a finger 8 is placed for inputting the fingerprint, living body potential deriving electrodes $2_1$ and $2_2$ provided on the surface of the fingerprint input sensor 1, for measuring the potential difference between two points of the muscle of the finger 8, a living body grounding electrode 3 disposed on one edge of the fingerprint input sensor 1, for grounding the living body, a living body data measuring unit 4 for amplifying signals 101 to 103 obtained from the living body potential deriving units $2_1$ and $2_2$ and the living body grounding electrode 3, a living body data analyzing unit 5 for digitizing and frequency analyzing living body data 104 measured in the living body data measuring unit 4, and a living body discriminating unit 6 for discriminating whether obtained data 105 is of a living body.

As the fingerprint input sensor 1 may be used "one-finger scanner" (a trade name) manufactured by Anritsu or a "finger only series" (a trade name) manufactured by NEC. The living body potential deriving electrodes $2_1$ and $2_2$ and the living body grounding electrode 3 may be formed from a conductive oxide compound, for instance ITO (indium tin oxide). As the living body data measuring unit 4 may be used "polygraph 60" (a trade name) manufactured by NEC medical system. As the living body data analyzing unit 5 and the living body discriminating unit 6 may be used a personal computer or a living body measuring/analyzing apparatus, such as an induced potential measuring apparatus "ER 1204" (a trade name) manufactured by NEC.

Figure 2:
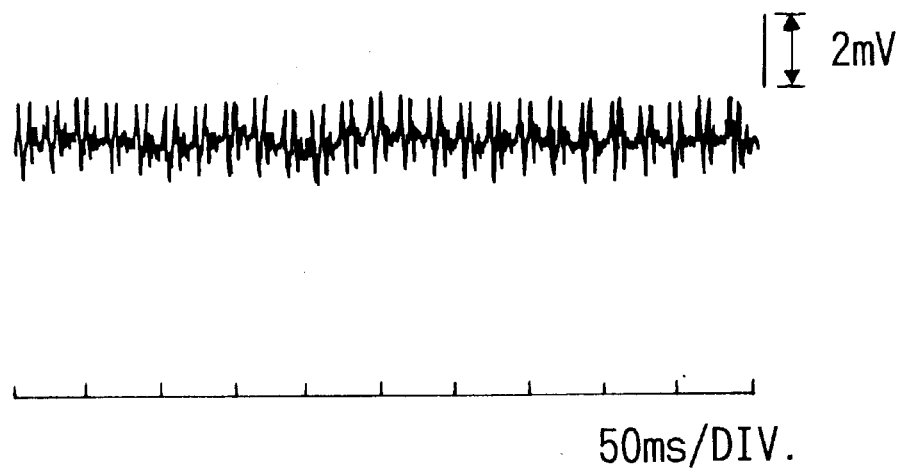
FIG. 2 is a view showing a waveform obtained when none of living body deriving electrodes $2_1$ and $2_2$ is touched.
Figure 3:
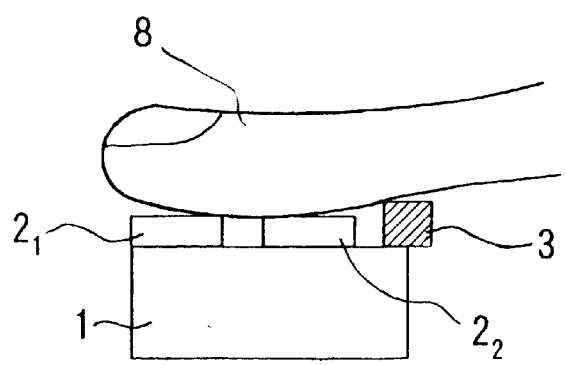
FIG. 3 is a view the state of contact between a replica finger 8 and living body deriving electrodes $2_1$ and $2_2$ and living body grounding electrode 3.
Figure 4:
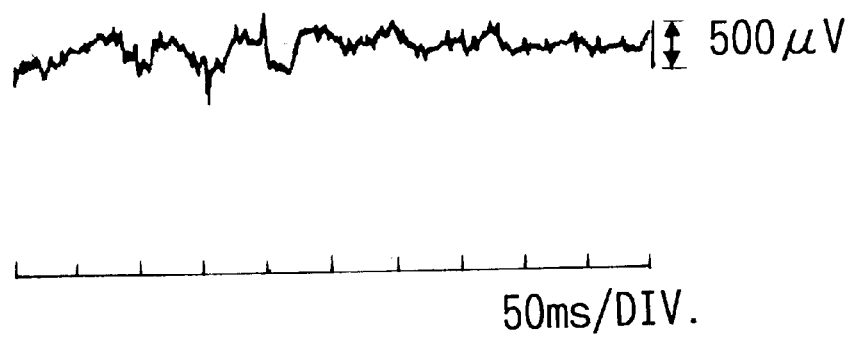
FIG. 4 is a view showing a waveform obtained from finger of living body.
Figure 5:
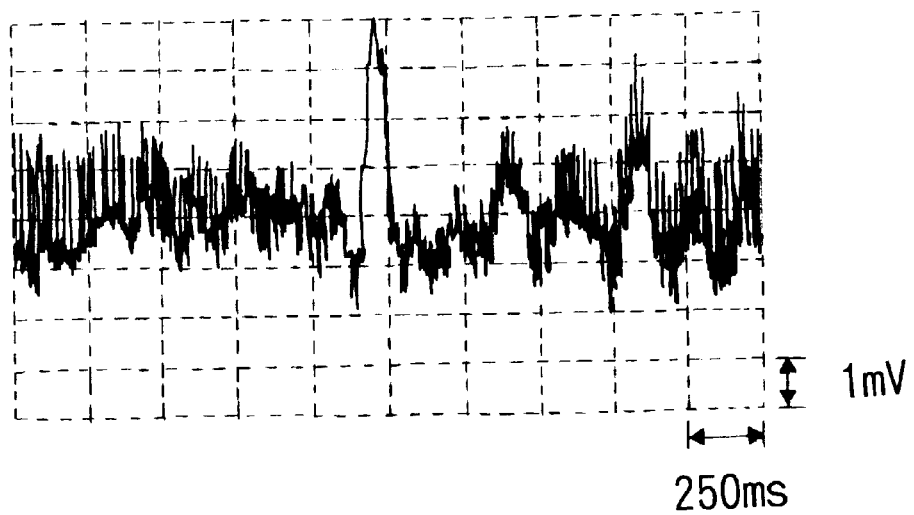
FIG. 5 is a view showing a waveform obtained from a replica finger.

The living body potential deriving electrodes $2_1$ and $2_2$ of the fingerprint sensor 1 are usually in contact with nothing, and a waveform as shown in FIG. 2 is obtained in a living body data measuring unit 4. When inputting the fingerprint, finger 8 which is a finger of a living body or a replica finger is placed on the fingerprint sensor 1. Thus, as shown in FIG. 3, the finger 8 is held in contact with the living body potential deriving electrodes $2_1$ and $2_2$ and the living body grounding electrode 3. The living body measuring unit 4 takes differences of the signals 101 to 103 from the living body potential deriving electrodes $2_1$ and $2_2$ and the living body grounding electrode 3, i.e., the difference between the finger muscle potential signals 101 and 103 and the difference between the signals 102 and 103 as well as the difference between these differences, and outputs the differences as living body difference potential data 104. In the case of the finger of the living body, a waveform as shown in FIG. 4 is obtained in the living body data measuring unit 4. In the case of the replica finger, a waveform shown in FIG. 5 is obtained from the living body data measuring unit 4. As is apparent from FIGS. 4 and 5, the waveforms of the finger of the living body and the replica finger are greatly different in amplitude and frequency from each other. In the case of the finger of the living body, as soon as the finger is placed on the fingerprint input sensor 1, the potential is reduced, then immediately thereafter the potential difference is increased once, and subsequently a stable potential difference is obtained. The living body data analyzer 5 performs frequency analysis of the living body data potential difference 104. The living body discriminating 6 judges, from the result 105 of analysis in the living body data analyzing unit 5, whether the living body potential difference data 104 is of muscle potential variations of a living body or potential variations of something other than a living body, thereby discriminating the finger 8 to be of the living body or the replica finger. The voltage range of the usual muscle potential is 10 $\mu$V to 10 mV. However, the fingerprint potential variation of the finger due to fingerprint input movement (i.e., which of a finger portion close to the muscle and a finger portion close to the finger tip first touches the electrode), is up to considerably low levels in the range. The frequency is 2 Hz to 2 kHz. These data cat be artificially forged as well as being obtainable from the living body. However, it is impossible to show potential variations corresponding to living body data in a series of a person's operations.

Figure 6:
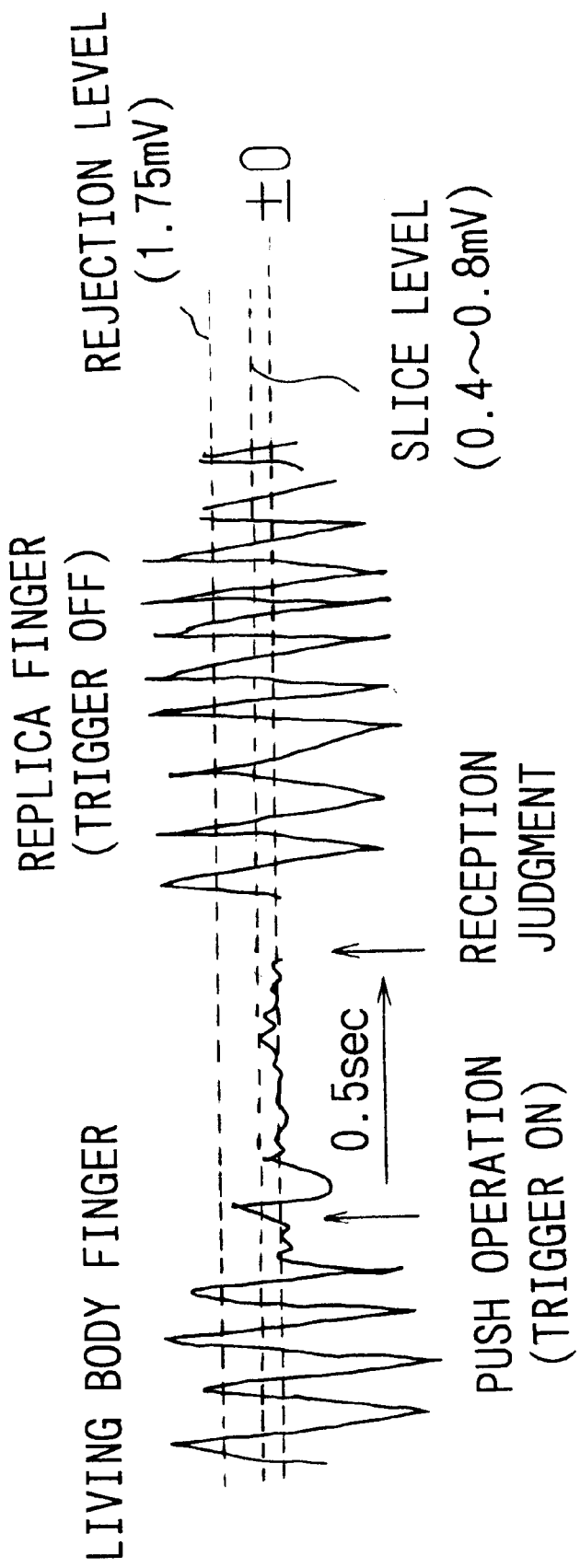
FIG. 6 is a view showing the principles underlying living body discrimination.

In the living body data analyzing unit 5, an instant when a certain potential level (for instance 1.75 mV) is exceeded with potential increase immediately after the finger has been put is set as a trigger point, and a subsequent threshold level is set to, for instance, 0.8 mV. When the potential data exceeds the level for the trigger and does not exceed the threshold level in 0.5 second (FIG. 6), the analysis of living body data is possible. In this case, the living body discriminating unit 6 determines the data is of living body reactions. Under this principle, the living body analysis is impossible for the replica because the potential level for the trigger exceeds the level, and exceeds it thereafter. It is thus automatically discriminated that the data is not of any living body.

Figure 7:
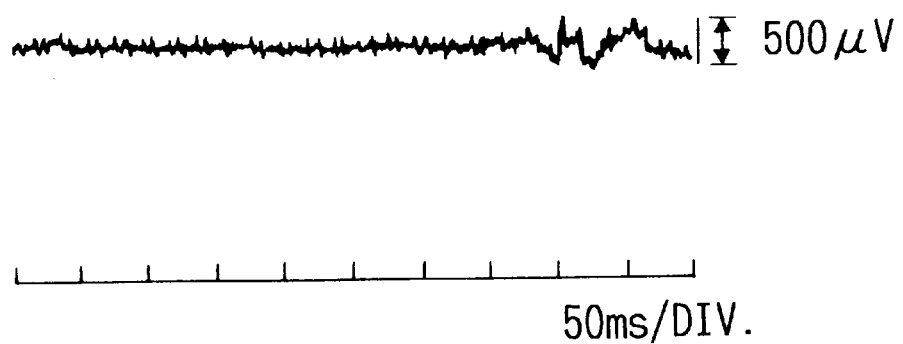
FIG. 7 is a view showing a small potential difference waveform obtained form finger of living body.

By putting the finger 8 of the living body on the fingerprint sensor 1, usually a waveform as shown in FIG. 4 is obtainable. When the skin is dry, however, a small potential difference waveform may be obtained as shown in FIG. 7. In this case, the potential difference does not exceed the potential level for the trigger right after putting the finger 8 on the fingerprint input sensor 1, so that no living body data analysis is performed. For this reason, when the potential difference fails to exceed the potential level for the trigger in the living body data analyzing unit 5, a new potential level (of 1 mV, for instance) for the trigger is set, and also a new threshold level is set to, for instance, 0.4 mV, according to potential differences measured by putting the finger a plurality of times in trial. By performing these new settings, it is possible to perform the living body data analysis, which permits living body discrimination.

Figure 8:
FIG. 8 is a view showing a frequency power spectrogram of a potential waveform obtained from finger of living body.
Figure 9:
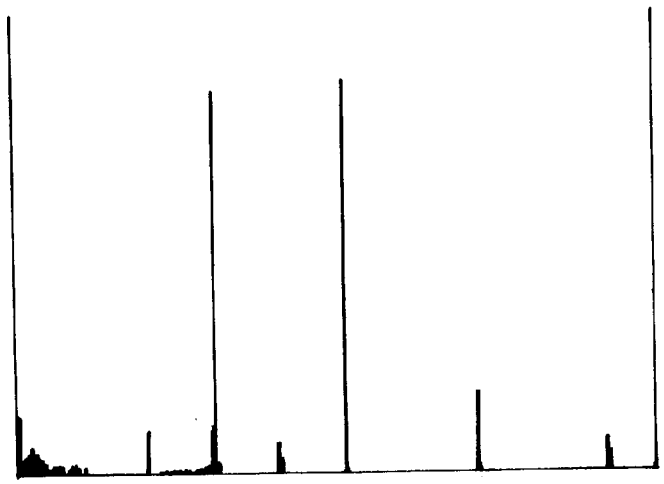
FIG. 9 is a frequency power spectrogram showing a potential waveform obtained from a replica finger.

When a replica finger, which is made of a material having a resistance close to that of the finger of the living body, is put on the fingerprint input sensor 1, the potential difference may exceed the potential level for the trigger, and the subsequent potential level may be held within the threshold level. In this case, when frequency analysis (for instance FFT) is applied to the obtained potential waveform, power spectrographs as shown in FIGS. 8 and 9 are respectively obtained in the case of the finger of the living body and the case of the replica finger. In the case of the finger of the living body, the frequency band is very broad. In the case of the replica, on the other hand, the data is concentrated in a low frequency band, and power is observed only at certain frequencies in a high frequency band. These power spectrographs indicate a difference of the a phenomenon peculiar to the living body based on slight vibrations thereof from the replica. The living body and the replica may be discriminated from one another by utilizing these phenomena and removing a power spectrum in a particular frequency band from the overall power spectrograph.

Figure 10:
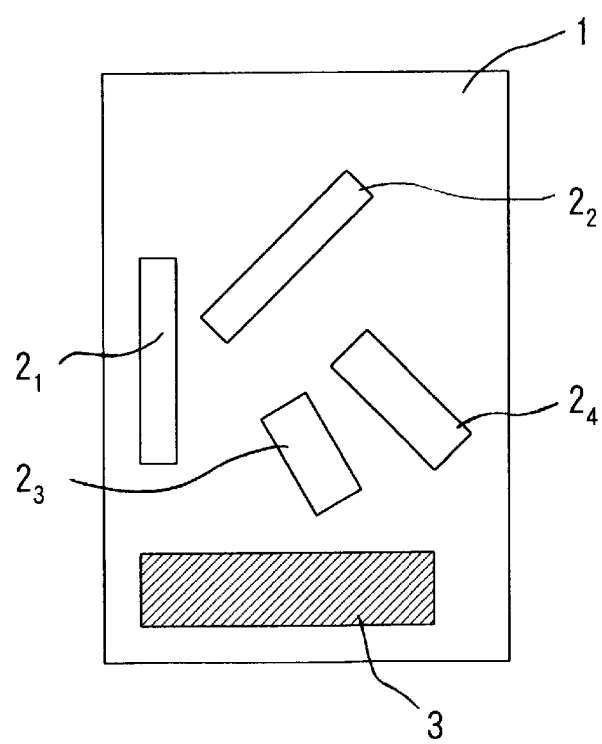
FIG. 10 is a schematic representation of a second embodiment of the living body discriminating apparatus according to the present invention.
Figure 11:
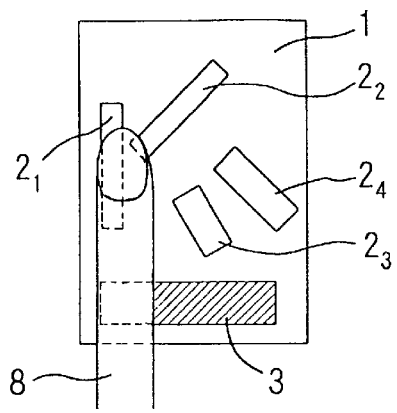
FIG. 11 is a view showing an example of the manner of putting finger in the second embodiment.
Figure 12:
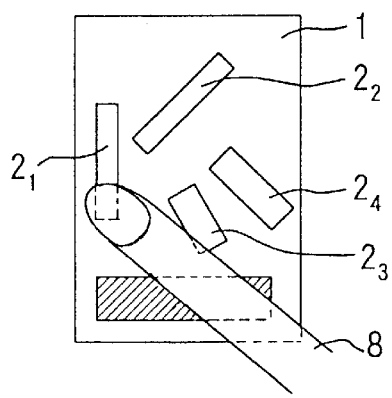
FIG. 12 is a view showing an example of the manner of putting finger in the second embodiment.

FIG. 10 shows a second embodiment of the living body discriminating apparatus according to the present invention. In this embodiment, three or more (i.e., four in this embodiment) living body potential deriving electrodes $2_1$ to $2_4$, are mounted on fingerprint input sensor 1. As shown in FIGS. 11 and 12, when the finger 8 is put on the fingerprint input sensor 1 is in contact with two of the four living body potential deriving electrodes $2_1$ and $2_4$, the living body data measurement is possible, and the living body discrimination can be performed as described before in the first embodiment.

Figure 13:
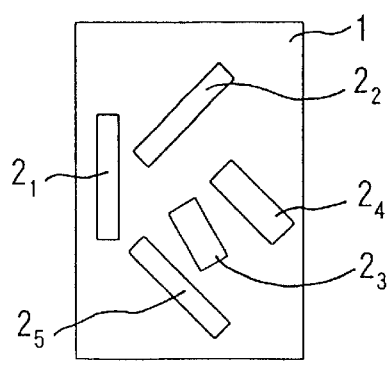
FIG. 13 is a schematic representation of a third embodiment of the living body discriminating apparatus according to the present invention.
Figure 14:
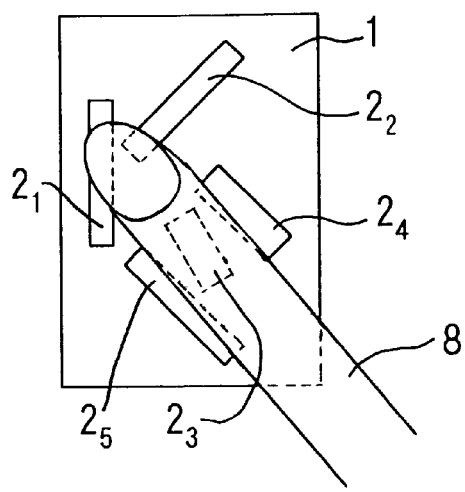
FIG. 14 is a view showing an example of the manner of putting finger in the third embodiment.

FIG. 13 shows a third embodiment of the living body data discriminating apparatus according to the present invention. In this case, three or more (i.e., five in this embodiment) living body potential deriving electrodes $2_1$ to $2_5$ are mounted on the fingerprint input sensor 1, and one of them is used as a living body grounding electrode. As shown in FIG. 14, when the finger 8 put on the fingerprint input sensor 1 is in contact with three of the five living body potential deriving electrodes $2_1$ to $2_5$, living body data measurement is possible, and the living body discrimination can be performed as described before in the first embodiment.

Figure 15:
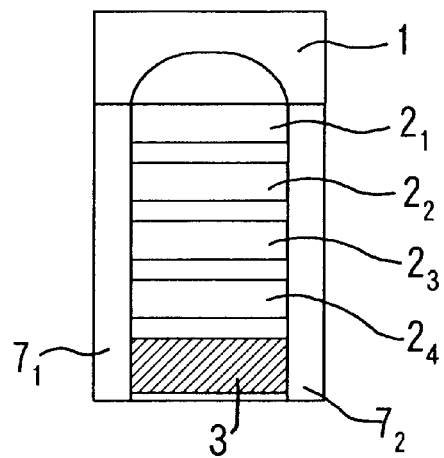
FIG. 15 is a schematic representation of a fourth embodiment of the living body discriminating apparatus according to the present invention.

FIG. 15 shows a fourth embodiment of the living body discriminating apparatus according to the present invention. In this embodiment, finger guides $7_1$ and $7_2$ are mounted on fingerprint input sensor 1 and living body potential deriving electrodes $2_1$ to $2_4$. With this arrangement, the finger 8 put on the fingerprint input sensor 1 is not deviated from the living body deriving electrodes $2_1$ to $2_4$. Thus, the living body discrimination can be made as described before in connection with the first embodiment.

As has been described in the foregoing, according to the present invention it is possible to perform discrimination as to whether the finger at the time of inputting the fingerprint is of the living body, which is useful for preventing the inputting of a forged fingerprint.

Changes in construction will occur to those skilled in the art and various apparently different modifications and embodiments may be made without departing from the scope of the present invention. The matter set forth in the foregoing description and accompanying drawings is offered by way of illustration only. It is therefore intended that the foregoing description be regarded as illustrative rather than limiting.

What is claimed is:

1. A living body discriminating apparatus comprising:
    fingerprint input sensor means on which a finger is placed when inputting fingerprint;
    a plurality of living body potential deriving means disposed as transparent sensors on the surface of the fingerprint input sensor means for measuring the potential difference between two muscle points of the finger;
    living body grounding electrode means provided on the fingerprint input sensor means for grounding the living body;
    living body data measuring means for amplifying signals obtained from the living body potential deriving means and the living body grounding electrode means;

living body data analyzing means for performing potential measurement and frequency analysis of living body data obtained in the living body data measuring means by digitizing the data; and living body discriminating means for discriminating whether the data obtained by processing in the living body data analyzing means is of the living body.

2. The living body discriminating means according to claim 1, wherein three elements are provided as the living body potential deriving means, two of the three elements being used to measure the potential difference between two muscle points of the finger, the remaining one of the elements being used as a living body grounding electrode.

3. The living body discriminating apparatus according to claim 1, wherein the fingerprint input sensor means has a finger guide for holding the finger at a constant position.

4. A living body discriminating apparatus, comprising:

a fingerprint sensor on which a finger is placed for inputting a fingerprint of the finger;

at least two living body potential deriving electrodes, provided on a surface of the fingerprint input sensor, for measuring the potential difference between two points of the muscle of the finger;

a living body ground electrode, disposed on the fingerprint input sensor, for grounding the living body;

a living body data measuring unit for amplifying signals obtained from the living body potential deriving electrodes and the living body grounding electrode;

a living body data analyzing unit for digitizing and frequency analyzing living body data measured in the living body data measuring unit; and a living body discriminating unit for discriminating whether obtained data is of a living body based on the analyzed result of the living body data analyzing unit, wherein the living body data measuring unit measures differences of the signals from the two living body potential deriving electrodes and the living body grounding electrode, and a difference between the two differences.

5. A living body discriminating apparatus, comprising:

a fingerprint sensor on which a finger is placed for inputting a fingerprint of the finger;

at least two living body potential deriving electrodes provided on a surface of the fingerprint input sensor, for measuring the potential difference between two points of the muscle of the finger;

a living body ground electrode disposed on the fingerprint input sensor, for grounding the living body;

a living body data measuring unit for amplifying signals obtained from the living body potential deriving electrodes and the living body grounding electrode;

a living body data analyzing unit for digitizing and frequency analyzing living body data measured in the living body data measuring unit; and a living body discriminating unit for discriminating whether obtained data is of a living body based on the analyzed result of the living body data analyzing unit, wherein the discrimination of the living body discriminating unit is performed based on the voltage amplitude and frequency range of the analyzed result of the living body data analyzing unit, and wherein the voltage range is 10 $\mu$V to 10 mV and the frequency is 2 Hz to 2 kHz.

6. A living body discriminating apparatus, comprising:

a fingerprint sensor on which a finger is placed for inputting a fingerprint of the finger;

at least two living body potential deriving electrodes provided on a surface of the fingerprint input sensor, for measuring the potential difference between two points of the muscle of the finger;

a living body ground electrode disposed on the fingerprint input sensor, for grounding the living body;

a living body data measuring unit for amplifying signals obtained from the living body potential deriving electrodes and the living body grounding electrode;

a living body data analyzing unit for digitizing and frequency analyzing living body data measured in the living body data measuring unit; and a living body discriminating unit for discriminating whether obtained data is of a living body based on the analyzed result of the living body data analyzing unit, wherein the discrimination is performed when the potential difference exceeds a first threshold level and does not exceed a second threshold level within a predetermined time period after the first threshold level was exceeded.

7. The living body discriminating means according to claim 6, wherein the frequency data is obtained by removing a power spectrum in a particular frequency band from an overall power spectrum that is obtained by frequency analyzing the living body data as performed by the living body data analyzing unit.

8. The living body discriminating apparatus, comprising:

a fingerprint sensor on which a finger is placed for inputting a fingerprint of the finger;

at least two living body potential deriving electrodes provided on a surface of the fingerprint input sensor, for measuring the potential difference between two points of the muscle of the finger;

a living body ground electrode disposed on the fingerprint input sensor, for grounding the living body;

a living body data measuring unit for amplifying signals obtained from the living body potential deriving electrodes and the living body grounding electrode;

a living body data analyzing unit for digitizing and frequency analyzing living body data measured in the living body data measuring unit; and a living body discriminating unit for discriminating whether obtained data is of a living body based on the analyzed result of the living body data analyzing unit, wherein the living body potential deriving electrodes are transparent.

* * * * *